(12) United States Patent
Forrester et al.

(10) Patent No.: US 8,980,617 B2
(45) Date of Patent: Mar. 17, 2015

(54) YEAST STRAINS FOR IMPROVED ETHANOL PRODUCTION

(71) Applicant: Pioneer Hi Bred International, Inc., Johnston, IA (US)

(72) Inventors: Kimberly J. Forrester, Ankeny, IA (US); William Rutherford, Grimes, IA (US); Douglas Haefele, Johnston, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 0 days.

(21) Appl. No.: 13/762,611

(22) Filed: Feb. 8, 2013

(65) Prior Publication Data
US 2013/0149760 A1 Jun. 13, 2013

Related U.S. Application Data

(63) Continuation of application No. 12/853,796, filed on Aug. 10, 2010, now Pat. No. 8,394,622.

(51) Int. Cl.
| | |
|---|---|
| *C12N 1/00* | (2006.01) |
| *C12P 7/06* | (2006.01) |
| *C12N 15/81* | (2006.01) |
| *C12R 1/865* | (2006.01) |

(52) U.S. Cl.
CPC . *C12N 15/81* (2013.01); *C12P 7/06* (2013.01); *C12R 1/865* (2013.01); *Y02E 50/17* (2013.01)

USPC .......... 435/255.2; 435/161; 435/254.11; 435/254.21

(58) Field of Classification Search
None
See application file for complete search history.

(56) References Cited

U.S. PATENT DOCUMENTS

2005/0069998 A1  3/2005 Ballesteros Perdices et al.

FOREIGN PATENT DOCUMENTS

WO  2007/145912 A1  12/2007

OTHER PUBLICATIONS

Kirasree, N., et al, "Characterisation of thermotolerant, ethanol tolerant fermentative *Saccharomyces cerevisiae* for ethanol production," Bioprocess Engineering, 2000, pp. 243-246.

Shi, D, et al, "Genome shuffling to improve thermotolerance, ethanol tolerance and ethanol productivity of *Saccharomyces cerevisiae*," J Ind Microbiol Biotech, 2009, vol. 36, pp. 139-147.

*Primary Examiner* — Iqbal H Chowdhury
(74) *Attorney, Agent, or Firm* — Pioneer Hi-Bred Int'l Inc

(57) ABSTRACT

Novel strains of yeast and methods for improved ethanol production utilizing the yeast strains are disclosed. In particular, the novel yeast strains *Saccharomyces cerevisae* YE1358 and YE1615 provide for increased fermentation temperature tolerance, as well as tolerance to increased levels of glucose and ethanol, and thereby provide increased ethanol production as compared to ethanol industry standard strains of *Saccharomyces cerevisae*. The novel yeast strains also generate decreased residual glucose than the ethanol industry standard yeasts.

16 Claims, 16 Drawing Sheets

YEAST STRAINS FOR IMPROVED ETHANOL PRODUCTION

CROSS-REFERENCE TO RELATED APPLICATIONS

This application is a continuation of U.S. patent application Ser. No. 12/853,796 filed Aug. 10, 2010 which claims the benefit of U.S. Provisional Patent Application No. 61/232,673, filed Aug. 10, 2009, which is hereby incorporated herein in its entirety by reference.

FIELD OF THE INVENTION

This invention relates to ethanol production processes and to isolated novel yeast strains and use of the same for improved methods of ethanol production.

BACKGROUND OF THE INVENTION

Increasing demand for renewable energy sources, including ethanol production, has created commercial demand for the generation of ethanol fuel sources. The process to obtain ethanol generally involves the transformation of plant matter, usually sugars, into a distilled pure ethanol product, through either a wet or dry milling processes. Wet milling methods include various soaking steps to soften grains and separate the soluble starches (from the germ, fiber and protein components) for further treatment before alcohol production methods. Dry milling methods are most commonly used for ethanol production, involving the grinding of whole plant matter into meal (without fractionating or separating the various component parts of the starch, as is done with wet milling) and forming a slurry. Subsequently, the starch components of the slurry are converted into sugars, through the use of high temperatures and enzymes, to effectuate the conversion. Upon generation of a sugar source from the plant matter, the conversion to ethanol requires the use of an ethanol-producing microorganism, such as yeasts.

The ethanol-producing microorganism utilized in the fermentation process most often involves yeast added to the mixture to convert sugars to alcohol, which is then distilled, purified, and denatured to generate the ethanol end product. (U.S. Pat. No. 4,316,956). The majority of fuel ethanol is produced by a few distinct strains of yeast. These commercial yeast strains require a high tolerance to both sugars and ethanol in order to yield sufficient ethanol concentrations.

The various processes and method steps for producing ethanol are well known by those skilled in the art and are described in various references. Ethanol production includes at least the following processes or method steps, or combinations of the same: milling, liquefaction, saccharification, fermentation and distillation. (See e.g., U.S. Pat. Nos. 5,231,017 and 4,316,956, WO 94/08027, WO 92/20777). One skilled in the art can ascertain the process for production of ethanol, including for example, whether steps are carried out simultaneously.

Numerous improvements to the ethanol production process, including both the wet and dry milling processes, have been achieved by those skilled in the art. For example: genetic modifications to ethanol-producing microorganisms (see e.g. Shi et al, *J. Ind. Microbiol. Biotechnol.*, 36:139-47 (2009)); improving thermotolerance (see e.g. U.S. Publication No. 2005/0069998); and improved enzymatic processes and enzymes (see e.g. WO 2007/145912).

Despite improvements to methods of ethanol production, the process is complex and the significant commercial interest in ethanol creates a continued need to further improve the production process, including the ethanol-producing microorganisms utilized therein. Accordingly, improvements upon commercial yeasts strains are further necessary to enhance industrial production of ethanol. Ethanol-producing microorganisms, such as yeast, capable of improving ethanol production, as measured by the ability to produce increased ethanol yields, provide both significant economic and industrial advantages. Even slight improvements in ethanol production provide significant commercial benefits. For example, it is estimated that an increased ethanol yield of 1% (estimated as an additional 0.0271 gallons/bushel) generates a commercial value of $100 million dollars annually for the ethanol industry (estimated as $2.00/gallon ethanol).

Accordingly, enhanced methods for ethanol production involving novel, isolated ethanol-producing microorganisms, such as yeast strains, will enhance production and profitability of industrial ethanol production.

BRIEF SUMMARY OF THE INVENTION

The present invention provides isolated yeast strains collected from diverse environments and tested for improved ability to enhance ethanol production over industry standard yeast strains. Therefore, an embodiment of the invention is a biologically pure culture of YE1358, having NRRL Accession No. Y-50434 and a biologically pure culture of YE1615, having NRRL Accession No. Y-50433.

In one embodiment, isolated *Saccharomyces cerevisae* strains YE1358 and YE1615 enhance ethanol production, as demonstrated in the detailed description of the invention.

Embodiments of the invention further include methods for utilizing isolated yeast strains YE1358 and YE1615 for enhancing ethanol production through production of increased alcohol yields.

In another embodiment, isolated yeast strains YE1358 and YE1615 are thermotolerant. In a further embodiment, isolated yeast strains YE1358 and YE1615 are tolerant to increased levels of glucose and ethanol, in comparison to the current industry standard *Saccharomyces cerevisae* strains, resulting in increased ethanol production.

In yet another embodiment, ethanol production using yeast strains YE1358 and YE1615, with improved temperature, glucose and ethanol tolerance results in significantly decreased input costs for ethanol production and increased ethanol production.

The foregoing and other aspects of the invention will become more apparent from the following detailed description.

DETAILED DESCRIPTION OF THE PREFERRED EMBODIMENTS

Figure 1:
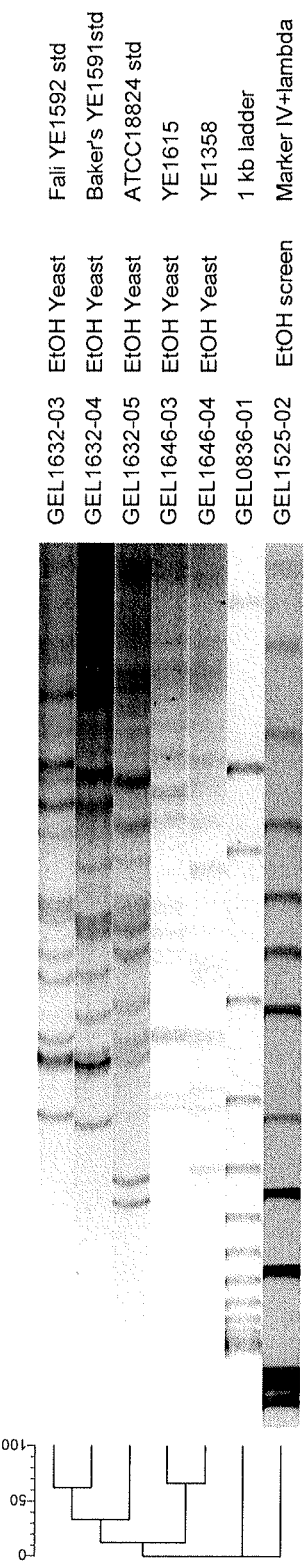
FIG. 1 shows genetic profiles of yeast strains YE1358, YE1615 and Commercial Yeast Strains.
Figure 2A:
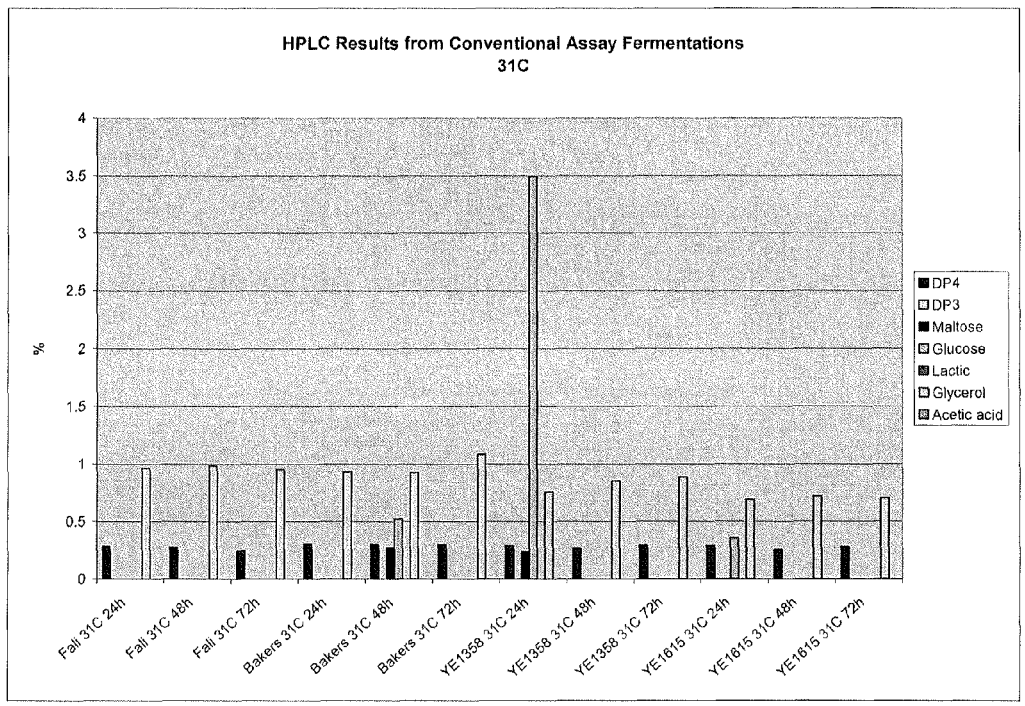
FIGS. 2A-2D show HPLC analysis of yeast fermentation at varying temperatures.
Figure 2B:
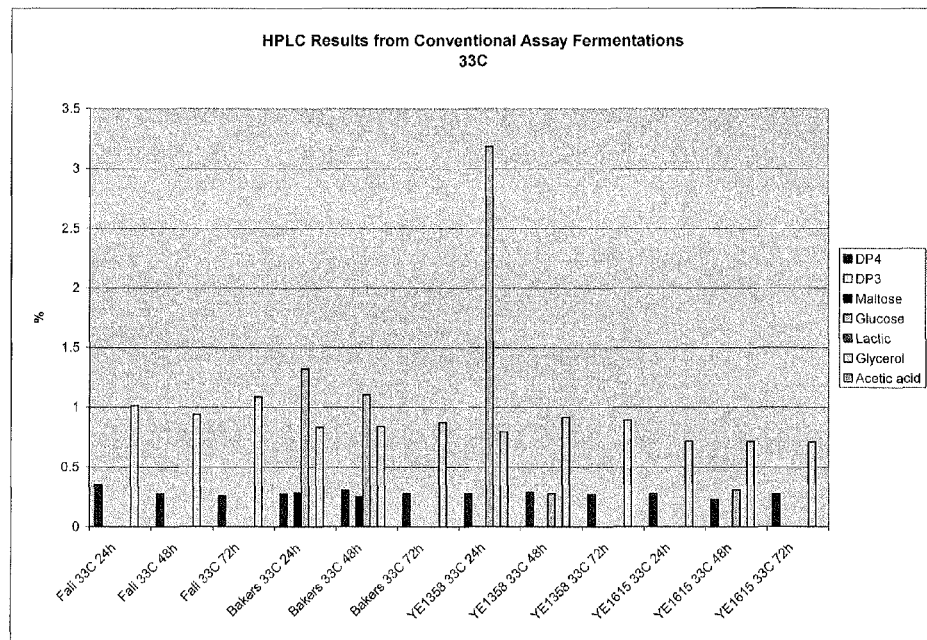
Figure 2C:
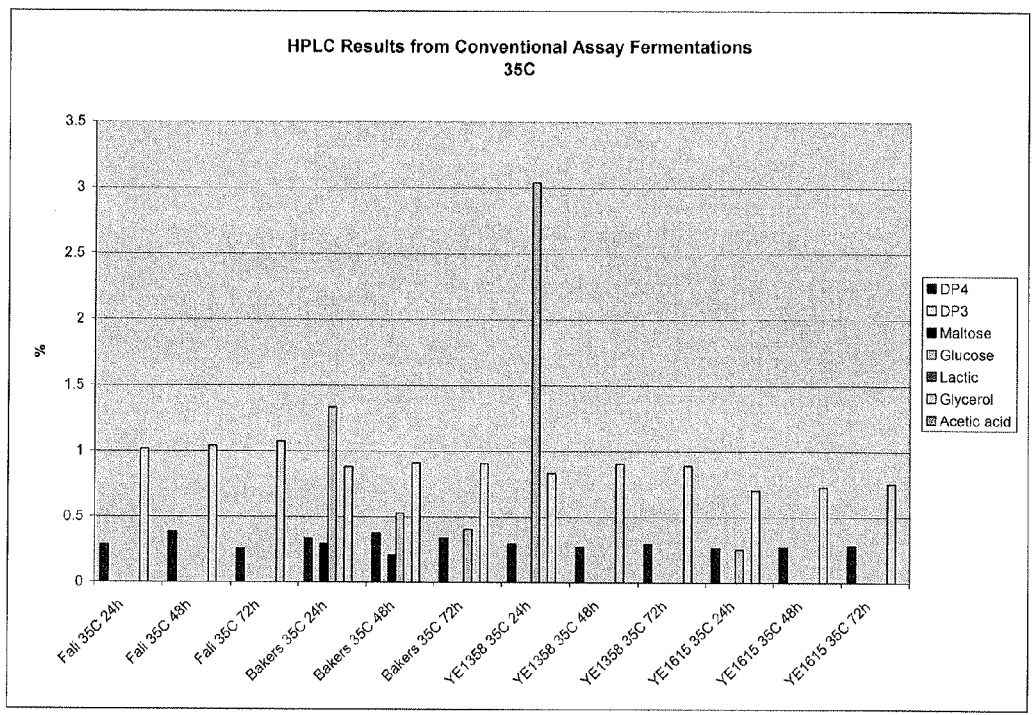
Figure 2D:
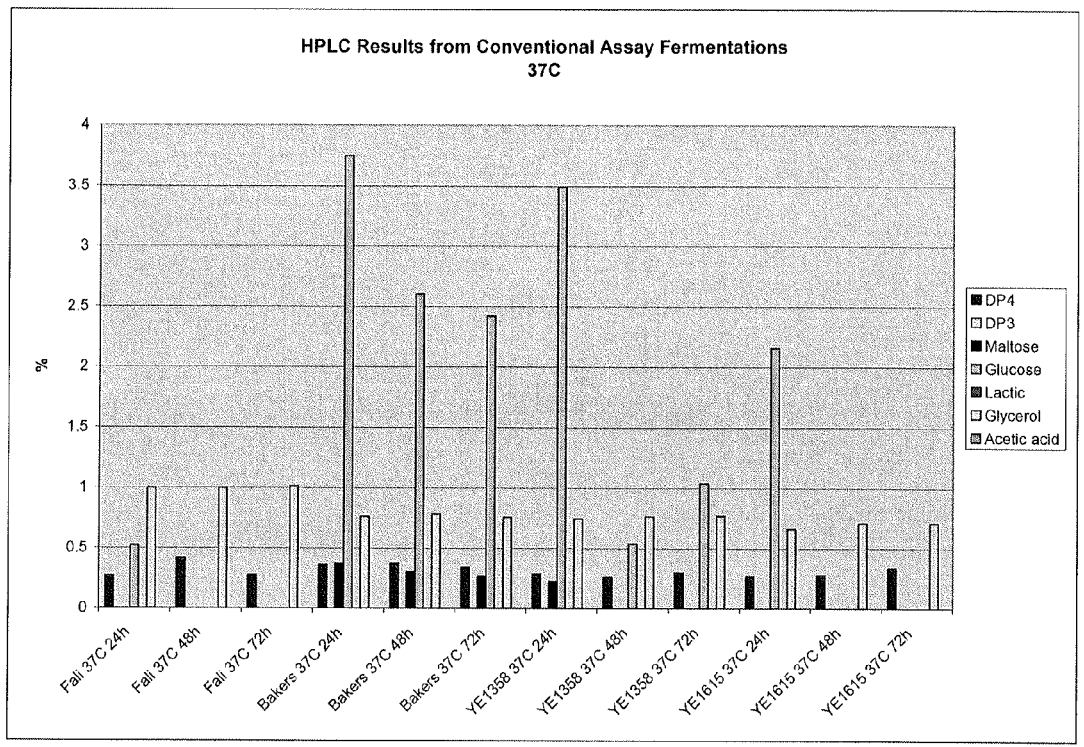

The embodiments of this invention are not limited to particular yeast strains or methods of improving ethanol production, which can vary as understood by skilled artisans. It is further to be understood that all terminology used herein is for the purpose of describing particular embodiments only, and is not intended to be limiting in any manner or scope. For example, as used in the specification and the appended claims, the singular forms "a," "an," and "the" can include plural referents unless the context clearly indicates otherwise. By way of example, "an element" means one or more elements. Further, all units, prefixes, and symbols may be denoted in their SI accepted form. Numeric ranges recited within the specification are inclusive of the numbers defining the range and include each integer within the defined range.

Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, of which the preferred materials and methods are described herein. In describing and claiming the embodiments of the present invention, the headings provided are not limitations to the embodiments of the invention and the following terminology will be used in accordance with the definitions set out below.

The term "alcohol (ethanol) tolerance" means an improved ability of a selected yeast strain to survive while maintaining function, such as producing ethanol, in a medium having a higher concentration of alcohol, as compared to other yeast strains.

The term "Commercial Yeast Strains" means commercially available active dry alcohol yeasts, including for example, Fali (Fleischmann's Yeast) and Baker's ethanol yeast. These strains represent the industry standard, traditionally demonstrating high alcohol tolerance, and thermotolerance, therefore producing maximum ethanol yields (up to 18% v/v (14.2% w/v), dependant on the fermentation methods). Commercial Yeast Strains were utilized for baseline measurements as representative of the current commercial microorganisms, preferably yeasts. The Commercial Yeast Strains are specifically *Saccharomyces*, such as the strain *Saccharomyces cerevisiae*.

The term "ethanol-producing microorganism" means any fermenting organism, including yeast, capable of producing ethanol from saccharides (mono- or oligo-). The term, as used herein, is synonymous with "ethanologenic microorganisms" and "fermenting organisms". A person of ordinary skill in the art can readily determine the effective amount of ethanol-producing microorganisms to be used in the methods of the present invention.

The term "fermentation" means the enzymatic and anaerobic breakdown of organic substances by microorganisms; such as the process by which sugars produce ethanol, carbon dioxide (waste product) and cellular energy. Although yeast ferments ethanol without oxygen, it is understood that the process may occur in the presence of oxygen as an aerobic process. Methods of fermentation and other ethanol-producing method steps (including separation of end products, distillation, purification and denaturation of ethanol) are well known in the art.

The term "glucose tolerance" means an improved ability of a selected yeast strain to survive while maintaining function, such as producing ethanol, in a medium having a higher concentration of glucose, as compared to other yeast strains.

The term "milling" means any process of breaking down grains into smaller particles. The term "dry milling" means any milling process whereby components of dry grain (whole) are not separated, such as bran and germ. The term "wet milling" means the milling process whereby component parts of grain are first separated.

The term "plant material" refers to all or part of any plant (e.g., cereal grains) and generally include a starch. For example, plant material may include maize, sorghum, barley, wheat, rye, rice, etc. and mixtures of plant materials or plant material byproducts.

The term "saccharification" refers to the process of converting starch to smaller polysaccharides and monosaccharides, including for example glucose. Methods of saccharification are well known by those skilled in the art to which the invention pertains.

The term "slurry" means an aqueous mixture of insoluble solids in the milling process for ethanol production.

The term "starch" means any complex polysaccharide carbohydrate plant material. "Plant material" means any part of the plant selected from any of the following, but not limited to the following, corn (*Zea mays*), wheat, sorghum, rice, millet, barley, potato, sugarcane and soybeans, and may include genetically modified varieties.

The term "strain" means any functional mutant or derivatives of the various yeast strains disclosed herein. For example, *Saccharomyces cerevisae* strain YE1358 (NRRL Accession No. Y-50432) and strain YE1615 (NRRL Accession No. Y-50433), which retain the functional activity of improving ethanol yield as described and defined by the methods and examples disclosed herein. Further, the term "functional mutant" means a yeast strain directly or indirectly obtained by genetic modification, of which may be achieved through any means, or using the referenced strains, and retaining the ethanol production, thermotolerance, glucose tolerance and ethanol tolerance properties of at least one of strains YE1358 and YE1615.

The term "thermotolerance" means an improved ability of a selected yeast strain to survive while maintaining function, such as producing ethanol, at increased temperatures, as compared to other yeast strains.

The term "yield" means generally the amount of end product, such as various types of ethanol (including for example fuel ethanol or industrial ethanol), distillers dried grains and distiller's dried grain plus solubles, produced using the methods set forth in the present invention. Yield can refer to the concentration, volume, percentage of increase, and other means of measuring end products. The preferred end product yield measured with the invention is an alcohol product, preferably ethanol, which may be separated and/or purified according to methods known to those of ordinary skill in the art. In some embodiments of the invention, the yield of ethanol using yeast strains YE1358 and YE1615 will be greater than at least 10.8%, 11%, 11.2%, 11.4% 11.6%, 11.8%, 12%, 12.2%, 12.4% 12.6%, 12.8%, 13%, 14.2%, 14.4% 14.6%, 14.8%, 15%, 15.2%, 15.4% 15.6%, 15.8%, 16, 16.1%, 16.2%, 16.3%, 16.4% 16.5%, 16.6%, 16.7%, 16.8%, 16.9%, 17% (v/v % ethanol production).

Isolated Yeast Strains

Isolated yeast strains *Saccharomyces cerevisae* YE1358 and YE1615 were deposited on Oct. 21, 2010 with the Agricultural Research Service (ARS) Culture Collection, housed in the Microbial Genomics and Bioprocessing Research Unit of the National Center for Agricultural Utilization Research (NCAUR), under the Budapest Treaty provisions. The strains were given the indicated accession numbers: *Saccharomyces cerevisae* YE1358, NRRL Accession No. Y-50432; and *Saccharomyces cerevisae* YE1615, NRRL Accession No. Y-50433. The address of NCAUR is 1815 N. University Street, Peoria, Ill., 61604. The deposits will irrevocably and without restriction or condition be available to the public upon issuance of a patent. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112. However, it should be understood that the availability of a deposit does not constitute a license to practice the subject invention in derogation of patent rights granted by government action. The deposit will be maintained without restriction in the NRRL Depository, which is a public depository, for a period of 30 years, or 5 years after the most recent request, or for the enforceable life of the patent, whichever is longer, and will be replaced if it ever becomes nonviable during that period.

Yeast strains YE1358 and YE1615 were isolated from inoculated and ensiled whole plant corn silage with high levels of dry matter. After significant experimentation the strains YE1358 and YE1615 were discovered from testing a collection of isolates. After isolation of the specific strains, taxonomic studies were done to identify the strains. The strains YE1358 and YE1615 were identified as *Saccharomyces cerevisae* and verified via DNA match reports (sequenced 323 base pairs from the D2 region of the Fungal 28S rRNA gene) (MIDI Labs, Delaware). Further, genetic profiles were generated (FIG. 1) using a modified yeast mitochondrial DNA restriction analysis and demonstrating genetic differences between all strains. (Querol et al., 1992: *Comparative Study of Different Methods of Yeast Strain Characterization System*, Appl. Microbiol. 15:439-46).

In embodiments of the invention, the enhanced ethanol-producing methods producing increased alcohol yields are accomplished by using the species *Saccharomyces* cerevisae as the ethanol-producing microorganism utilized in the fermentation process. The novel, isolated yeast strains YE1358 and YE1615, or compositions containing YE1358, YE1615 or closely related organisms, are used to enhance ethanol production. Those of ordinary skill in the art will know of various suitable alternative compositions for the isolated yeast strains YE1358 and YE1615, or compositions containing YE1358, YE1615 or closely related organisms using routine experimentation.

The activity associated with the invention may be found in other strains of *Saccharomyces cerevisae* and in other species of *Saccharomyces* and possibly in other genera. This can be established by routine experimentation, on the basis of the information provided herein relating to the invention.

Glucose and Ethanol Tolerance

In one embodiment, yeast strains YE1358 and YE1615 demonstrate superior glucose tolerance over expected tolerance levels. (Elsevier, 1984, Yeasts: A Taxonomic Study, 88). Glucose concentrations up to 60% can be utilized as growth media for yeast strains YE1358 and YE1615 without rate-limiting growth. These glucose tolerance levels far exceed the industrial ethanol fermentation standards of approximately 20% of fermentable sugar.

In another embodiment, yeast strains YE1358 and YE1615 demonstrate growth at ethanol concentrations up to 25%, exceeding the generally accepted ethanol concentration of 10-15%. Alcohol tolerance is a biologically limiting factor as yeast strains are inactivated and therefore stop metabolizing and growing when exposed to the inhibitory effects of increased levels of ethanol. The ethanol tolerance of strains YE1358 and YE1615 further exceeds even those ethanol tolerance levels achieved in studies demonstrating the "coaching" of ethanol tolerance up to 23%. (Lyons, 1999, Alcohol Textbook 3rd Ed., vol. 1). In still further embodiments of the invention, yeast strains YE1358 and YE1615 demonstrate enhanced growth at both 15% and 20% ethanol concentrations (with a 60% glucose concentration), where Commercial Yeasts Strains were unable to grow at 10% or greater ethanol concentrations (with a 60% glucose concentration), demonstrating an unexpected improvement over the alcohol tolerance of Commercial Yeast Strains.

In yet another embodiment, yeast strains YE1358 and YE1615 retain both the alcohol and glucose tolerance described herein, simultaneously with its thermotolerance as set forth in this detailed description of the invention. The improved tolerances of strains YE1358 and YE1615 further result in increased yields of ethanol, according to percentage of ethanol yield.

Thermotolerance

According to the invention, yeast strains YE1358 and YE1615 are capable of producing ethanol at increased temperatures due to thermotolerance. The demonstrated thermotolerance of yeast strains YE1358 and YE1615 allows at least maintained and increased production of ethanol at increasing temperatures which are generally regarded as those exceeding acceptable temperatures for fermentation with yeasts. Strains YE1358 and YE1615 produce increased ethanol yields in comparison to one or more Commercial Yeast Strains at temperature of at least above 31° C., 33° C., 35° C. and 37° C., contrary to the industry standard production which experience decreased ethanol production as temperatures increase, due to the inhibitory effects of ethanol on yeast with increased temperatures. (D'Amore et al., *Enzyme Microb. Technol.*, 11:411-16 (1989)).

Maintained and increased production of ethanol yields at higher fermentation temperatures results in—decreased expenditures for commercial ethanol plants. Thermotolerant yeasts provide numerous advantages; including energy savings due to a reduced need for cooling fermenters and other compensatory means to ensure the yeasts remain active. Therefore, it is economically and technically advantageous to ferment ethanol at higher temperatures and with thermotolerant yeast strains, including strains YE1358 and YE1615.

In yet another embodiment, yeast strains YE1358 and YE1615 retain thermotolerance simultaneously with ethanol and glucose tolerance, as set forth in this detailed description of the invention. These improved tolerances of strains YE1358 and YE1615 further result in increased yields of ethanol according to the present invention. These embodiments provide unexpected results of simultaneously maintaining ethanol, glucose, and thermotolerance, rather than showing a decrease in ethanol or glucose tolerance and, therefore, ethanol yields, as a result of increasing temperatures.

Ethanol Production

According to the invention, ethanol is the preferred end product from the claimed methods utilizing yeast strains YE1358 and YE1615. In preferred embodiments, the ethanol yield will exceed at least 10.8%, 11%, 11.2%, 11.4% 11.6%, 11.8%, 12%, 12.2%, 12.4% 12.6%, 12.8%, 13%, 14.2%, 14.4% 14.6%, 14.8%, 15%, 15.2%, 15.4% 15.6%, 15.8%, 16, 16.1%, 16.2%, 16.3%, 16.4% 16.5%, 16.6%, 16.7%, 16.8%, 16.9%, 17% (v/v % ethanol production). Ethanol yields generated from the claimed methods of the present invention are identified by high-pressure liquid chromatography (HPLC) analysis. In the preferred embodiments of the present invention, increased ethanol production results in decreased input costs and increased economic value obtained from ethanol production.

The fermentation required for ethanol production is ongoing until sufficient yields of ethanol are produced. Fermentation may be carried out over extended periods of time, for example for up to 24 hours to 96 hours. One of skill in the art may ascertain such variables of length of fermentation to produce desired ethanol yields while utilizing the yeast strains YE1358 and YE1615, according to the invention.

The invention provides methods for producing ethanol comprising culturing a yeast strain of the invention in a medium comprising a saccharide, particularly an aqueous medium. Preferably, the yeast strain is capable of increasing ethanol yields when compared to a Commercial Yeast Strain. More preferably, the yeast strain is selected from the group consisting of: *Saccharomyces cerevisae* strain YE1358 having NRRL Accession No. Y-50432; *Saccharomyces cerevisae* strain YE1615 having NRRL Accession No. Y-50433; and yeast strains, which are mutants or derivatives of strain YE1358 or strain YE1615, said mutants and derivatives comprising the ethanol production, thermotolerance, glucose tolerance, and ethanol tolerance properties of at least one of strains YE1358 and YE1615. The culturing is conducted at a temperature that is suitable for the growth and multiplication of the yeast stain as disclosed elsewhere herein. In addition to at least one saccharide, the medium can contain other components that promote the growth and multiplication of the yeast strain of interest. Such other components include, for example, amino acids, other nitrogen containing molecules, and one or more additional saccharides. Suitable media include, for example, media produced from corn, particularly corn grain.

The methods of the invention provide for increased ethanol production when compared to the culturing of a Commercial Yeast Strain under similar conditions. Such methods can generate an increase in ethanol yield of at least about 1%, 1.5%, or 2%, when compared to ethanol yield from a Commercial Yeast Strain cultured under the same conditions.

In another embodiment of the invention, increased ethanol production is further demonstrated by decreased residual glucose levels. Decreased residual glucose levels are desirable as an indicator of the extent of ethanol production. Ideal ethanol production methods would result in 0% remaining glucose and yield 100% ethanol. Utilizing 100% of the glucose sources enhances complete usage of the products and significantly decreases input costs to ethanol production methods. Yeast strains YE1358 and YE1615 have approached such ideal conditions, as demonstrated in the examples of the detailed description.

Yeast strains YE1358 and YE1615 yield lower residual glucose and higher ethanol amounts, as a result of increased glucose conversion to ethanol. In preferred embodiments of the present invention, yeast strains YE1358 and YE1615 yield residual glucose level less than 1%, and more preferably, residual levels less than 0.88%, and still more preferably, residual levels less than 0.35%. Further, yeast strains YE1358 and YE1615 yield residual glucose level less than Commercial Yeast Strains at temperatures greater than 31° C., more preferably at temperatures greater than 33° C., and even more preferably at temperatures greater than 35° C. or 37° C.

In yet another embodiment of the invention, increased ethanol production, as a result of decreased fermentation stress, is further demonstrated by decreased glycerol levels. Glycerol is an indicator of stress in the ethanol production methods, as it is a sugar source failing to convert to ethanol, further resulting in decreased ethanol yields. In a preferred embodiment of the invention, yeast strains YE1358 and YE1615 demonstrate low glycerol levels at increased temperatures of at least above 31° C., above 33° C., above 35° C., and above 37° C. In even more preferred embodiments, fermentation stress with yeast strains YE1358 and YE1615 is lower at increased temperatures.

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications to the embodiments of the invention to adapt it to various usages and conditions.

EXAMPLES

Example 1

Glucose and Ethanol Tolerance

Yeast strains were initially screened for glucose tolerance using the 96-well microtiter plate format. Yeast Nitrogen Base media (Difco) with varying levels of glucose concentration (up to approximately 60%) was utilized for the growth media and current Commercial Yeast Strains (Fali and Baker's yeast) served as baseline measurements. All plates demonstrated sufficient growth at all glucose levels and Commercial Yeast Strains grew at 60% glucose concentration.

Yeast strains were also screened for ethanol tolerance utilizing the same Yeast Nitrogen Base utilized for the growth media, with 60% glucose concentration and varying levels of ethanol concentration (up to approximately 25%). Commercial Yeast Strains did not grow at 10% or greater ethanol concentration with the 60% glucose concentration. Yeast strains *Saccharomyces cerevisae* YE1358 and YE1615 demonstrated either good growth or light growth at both 15% and 20% ethanol concentrations and 60% glucose concentration.

Example 2

Ethanol Production

Yeast collections were further screened for ethanol production using a colorimetric kit and ethanol UV-methods (Boehringer Mannheim/R-Biopharm Enzymatic BioAnalysis/Food Analysis). Commercially realistic growth media was utilized for ethanol production screening; High Moisture Corn broth (pH of 4.2) containing 2% glucose concentration and 1% 2M urea concentration. Multiple plates were grown at 30° C., 35° C., 40° C., and 45° C. and subsequently 24 hour and 72 hour readings were recorded. Several yeast strains, including yeast strains *Saccharomyces cerevisae* YE1358 and YE1615 isolates, produced an increased amount of ethanol in comparison to the Commercial Yeast Strain standards.

Example 3

Residual Glucose Levels

Assays for glycerol levels were also analyzed for the yeast strains, demonstrating low levels for all strains, including YE1358 and YE1615, indicative of low levels of fermentation stress. Strains YE1358 and YE1615 demonstrated lower residual glucose and higher ethanol amounts than both Commercial Yeast Strains, indicating increased glucose conversion to ethanol. None of the strains reached a 1% residual glucose level, indicative of incomplete fermentation. The HPLC results show a difference in the amount of byproduct acetic acid produced, indicating a heterogeneous metabolic conversion of glucose.

HPLC samples were collected at the final time point of 72 hours. (FIGS. 2A-2D). The residual sugar was lowest at 33° C. and trending towards increasing at 35° C. and 37° C. Only yeast strains YE1358 and YE1615 reached a residual glucose level below 1%, with 0.35% residual glucose for YE1358 and 0.88% residual glucose for YE1615, respectively. Additionally, glycerol levels remained low for all strains at the increased temperatures.

Example 4

Total Fermentables

The selected yeast isolates YE1615 and YE1358 were also twice analyzed by the Conventional High Total Fermentables Assay with the following methods. Corn grain substrate was dried and ground to 1 mm. The amounts of 25 g of ground corn, 73 g distilled water, 1 ml of 200 mM $CaCl_2$, and 1 ml of 2 M urea was added to a 250 ml Erlenmeyer flask. A sir bar was added and the pH was adjusted to 6.5 using 1M NaOH. Additionally, 100 µl of a-amylase enzyme was added. The flasks were covered and placed in boiling water baths and stirred for 15 minutes. The flasks were then placed in a 70° C. water bath to cool. Once cooled, the pH was adjusted to 4.5 with HCl and 600 µl of glucoamylase was added. The flasks were incubated while stirring at 50° C. for 1 hour. Then the flasks were cooled to 25° C. in a water bath and the sample yeast was added. The flasks were stoppered with a rubber stopper with a needle to release the $CO_2$ produced. The initial weight was recorded for each flask which were incubated at various temperatures. The flasks were stirred and their weight loss recorded at specified time points.

Figure 3A:
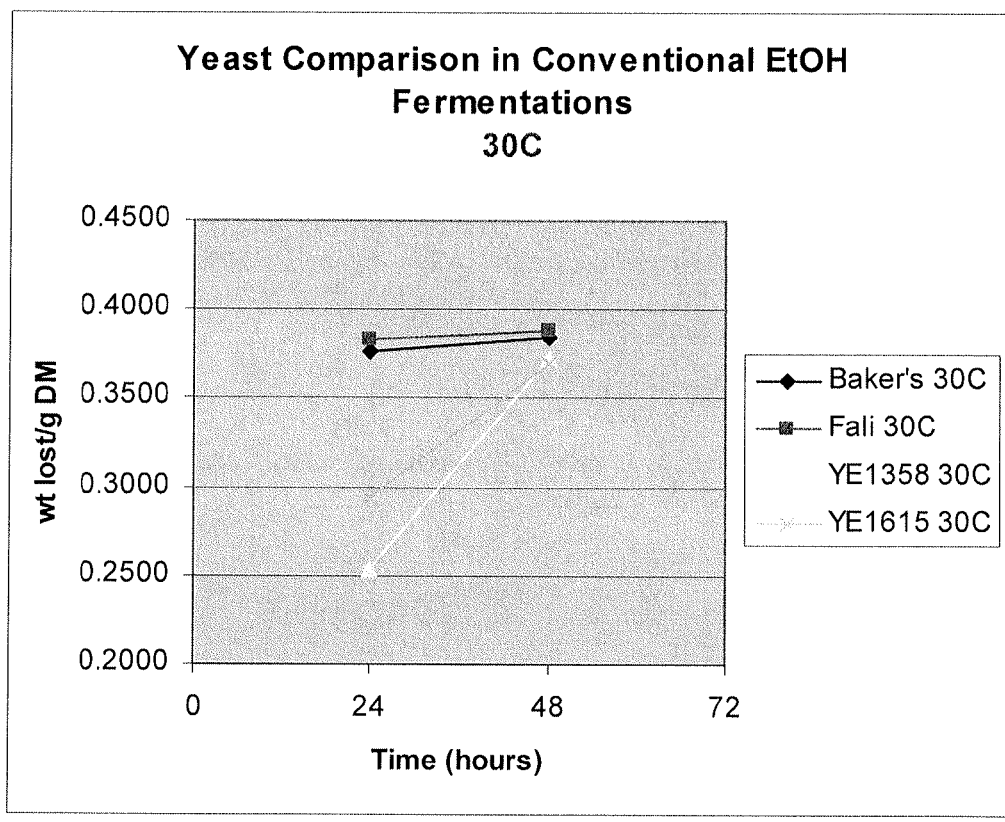
FIGS. 3A-3C show the effect of temperature on conventional ethanol fermentation of selected isolated yeast strains.
Figure 3B:
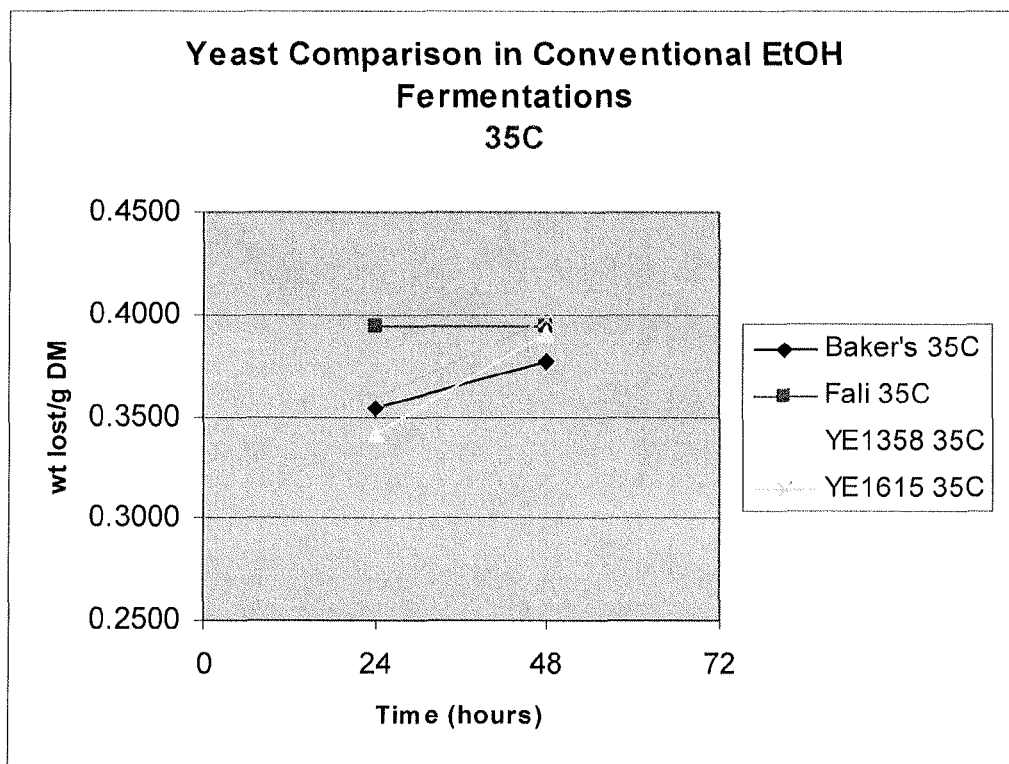
Figure 3C:
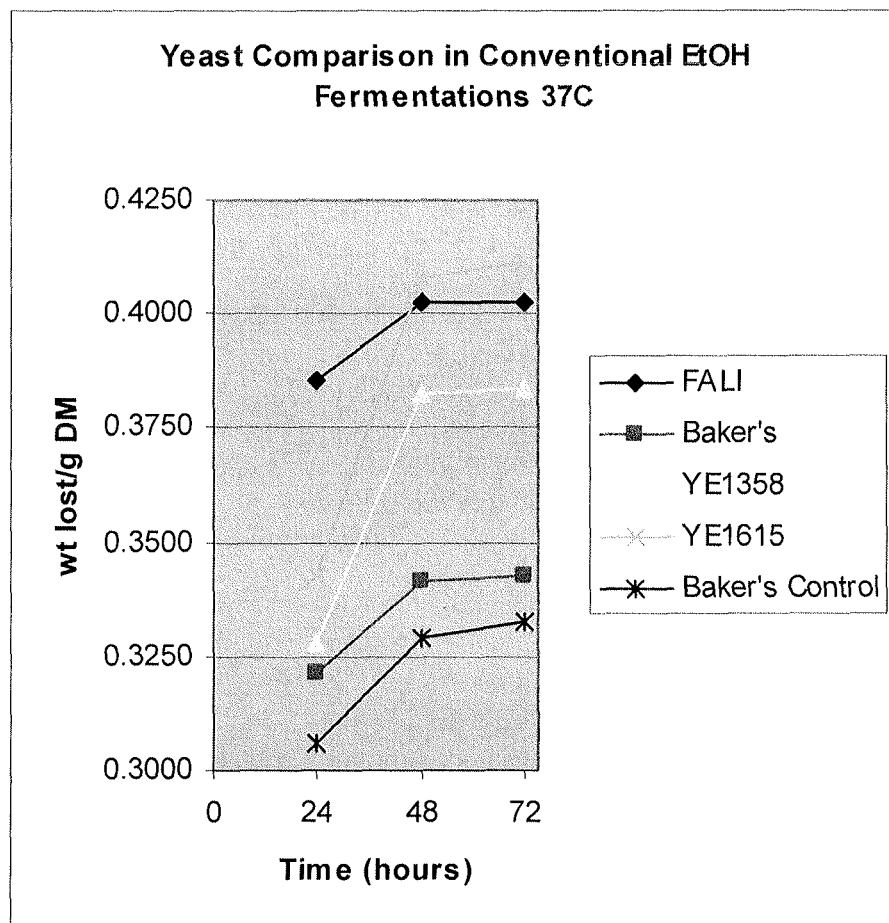

The Conventional High Total Fermentables Assay was completed at 30° C. and 35° C. The initial ending time point was 48 hours (See, Table 1). At 48 hours, Commercial Yeast Strains (both Baker's and Fali yeast) performed better at 30° C. in comparison to YE1615 and YE1358 yeast strains. However, at 35° C. YE1615 performed slightly better than a Commercial Yeast Strain (Fali), where as YE1358 was slightly lower than the Commercial Yeast Strain. Overall weight loss (ethanol production) was greatest at the increased temperature. (FIGS. 3A-3C).

TABLE 1

| Sample ID | Initial Wt | 24 hr Wt | 24 hr Wt Lost/g DM | Gal/BU | 48 hr wt | 48 hr wt lost/g DM | 48 hr gal/BU |
|---|---|---|---|---|---|---|---|
| Baker's (30° C.) | 253.88 | 245.57 | 0.372 | 2.817 | 245.22 | 0.3879 | 2.933142648 |
| Fali (30° C.) | 251.44 | 242.93 | 0.381 | 2.883 | 242.71 | 0.3907 | 2.954761978 |
| YE 1358 (30° C.) | 248.76 | 243.73 | 0.223 | 1.69 | 240.26 | 0.38 | 2.873714085 |
| YE 1615 (30° C.) | 250.99 | 244.91 | 0.271 | 2.053 | 242.41 | 0.3843 | 2.9057301 |
| Bakers (35° C.) | 251.75 | 244.45 | 0.328 | 2.48 | 244.02 | 0.3456 | 2.61342515 |
| Fali (35° C.) | 248.51 | 239.78 | 392 | 2.967 | 239.58 | 0.3996 | 3.022029206 |
| YE 1358 (35° C.) | 245.13 | 238.11 | 0.315 | 2.384 | 236.37 | 0.3923 | 2.96622042 |
| YE 1615 (35° C.) | 251.81 | 244.35 | 0.336 | 2.538 | 242.87 | 0.4009 | 3.031514692 |
| Baker's (30° C.) | 246.99 | 238.54 | 0.378 | 2.861 | 238.24 | 0.3915 | 2.960424987 |
| Fali (30° C.) | 226.81 | 218.2 | 0.385 | 2.915 | 218.06 | 0.3913 | 2.95924129 |
| YE 1358 (30° C.) | 243.74 | 237.78 | 0.266 | 2.01 | 235.27 | 0.379 | 2.865742489 |
| YE 1615 (30° C.) | 243.17 | 236.6 | 0.294 | 2.221 | 243.55 | 0.3862 | 2.92060602 |
| Baker's (35° C.) | 253.82 | 245.65 | 0.368 | 2.78 | 245.04 | 0.3935 | 2.975453082 |
| Fali (35° C.) | 252.24 | 243.43 | 0.397 | 3.002 | 243.31 | 0.4006 | 3.029299525 |
| YE 1358 (35° C.) | 246.89 | 239.01 | 0.354 | 2.674 | 238.07 | 0.3943 | 2.981996586 |
| YE 1615 (35° C.) | 255.29 | 247.15 | 0.366 | 2.768 | 246.34 | 0.4009 | 3.031299159 |
| Baker's (30° C.) | 246.35 | 237.97 | 0.375 | 2.839 | 237.54 | 0.3945 | 2.983346404 |
| Fali (30° C.) | 244.07 | 235.52 | 0.384 | 2.901 | 235.25 | 0.3955 | 2.990362909 |
| YE 1358 (30° C.) | 244.86 | 238.74 | 0.274 | 2.069 | 236.38 | 0.3802 | 2.874918462 |
| YE 1615 (30° C.) | 253.89 | 246.78 | 0.318 | 2.407 | 245.23 | 0.3882 | 2.935493865 |
| Baker's (35° C.) | 261.74 | 253.61 | 0.366 | 2.769 | 253.06 | 0.3893 | 2.943532268 |
| Fali (35° C.) | 250.89 | 242.13 | 0.394 | 2.981 | 241.99 | 0.3988 | 3.015380293 |
| YE 1358 (35° C.) | 248.35 | 240.46 | 0.354 | 2.6 | 239.5 | 0.396 | 2.994649553 |
| YE 1615 (35° C.) | 259.09 | 250.78 | 0.373 | 2.824 | 250.21 | 0.3974 | 3.004916923 |

Figure 4A:
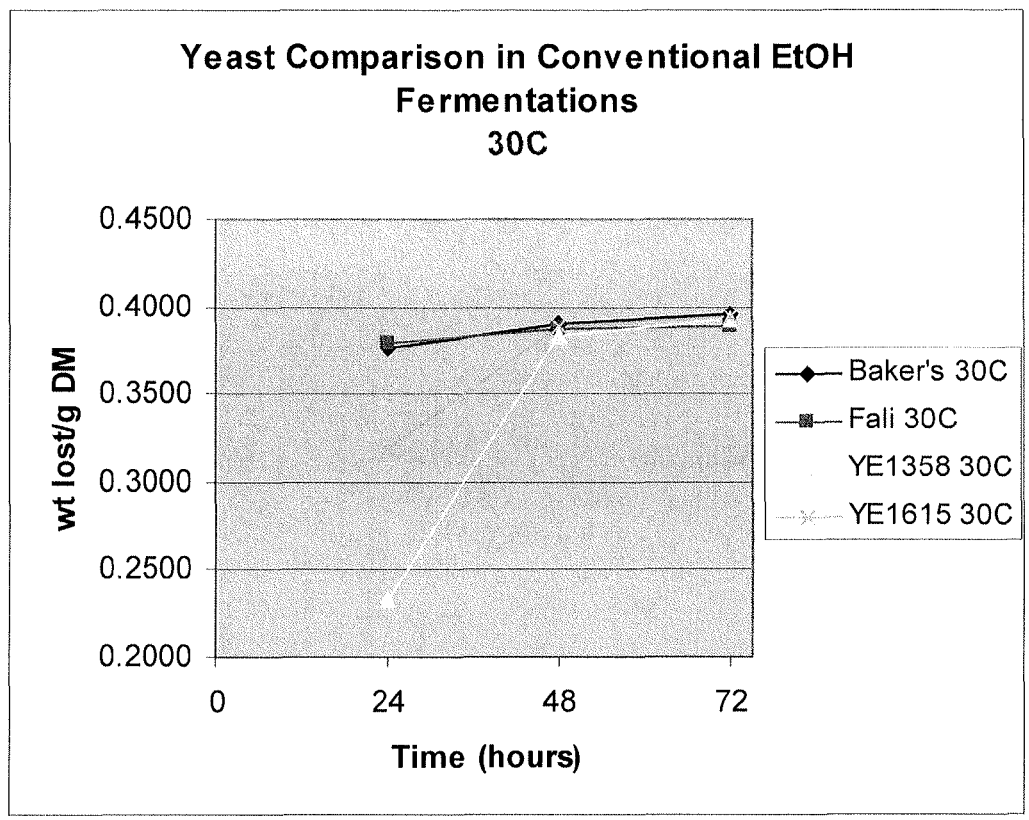
FIGS. 4A-4B show the effect of temperature on conventional ethanol fermentation.
Figure 4B:
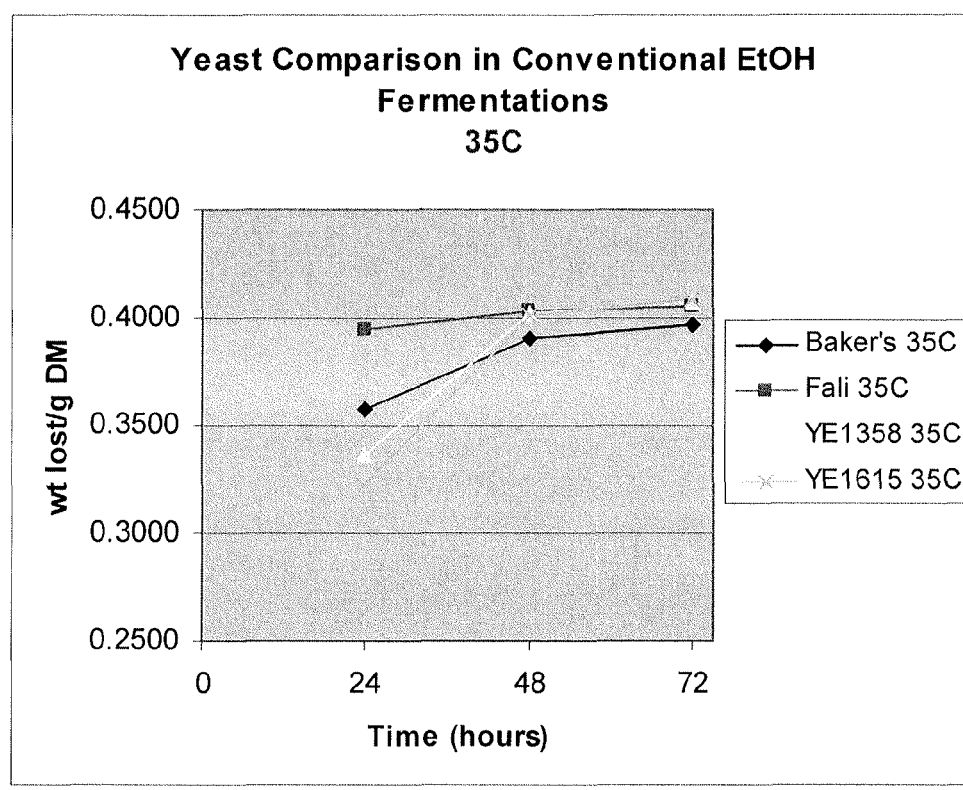

The ending time was subsequently extended to 72 hours. At 72 hours, a Commercial Yeast Strain (Baker's yeast) performed slightly better than the isolated yeast strains at 30° C. However, at 35° C. both YE1615 and YE1358 yeast strains out performed both Commercial Yeast Strains. Additionally, at 37° C. YE1615 out performed both Commercial Yeast Strains and YE1358 out performed Baker's yeast for ethanol production. Overall weight loss (indicative of ethanol production) was greatest at the increased temperature of 37° C. (FIGS. 4A-4B; Table 2).

TABLE 2

| Sample ID | Average 24 Hr. Wt Loss | Average 48 Hr. Wt Loss | Average 72 Hr. Wt Loss |
|---|---|---|---|
| Baker's (30° C.) | 0.3763 | 0.3905 | 0.3953 |
| Fali (30° C.) | 0.3795 | 0.3870 | 0.3890 |

TABLE 2-continued

| Sample ID | Average 24 Hr. Wt Loss | Average 48 Hr. Wt Loss | Average 72 Hr. Wt Loss |
|---|---|---|---|
| YE1358 (30° C.) | 0.2327 | 0.3830 | 0.3931 |
| YE1615 (30° C.) | 0.3184 | 0.3885 | 0.3941 |
| Bakers (35° C.) | 0.3572 | 0.3905 | 0.3969 |
| Fali (35° C.) | 0.3945 | 0.4030 | 0.4054 |
| YE1358 (35° C.) | 0.3361 | 0.4026 | 0.4073 |
| YE1615 (35° C.) | 0.3225 | 0.4007 | 0.4083 |
| Baker's (37° C.) | 0.3213 | 0.3417 | 0.3426 |
| Fali (37° C.) | 0.3855 | 0.4023 | 0.4025 |
| YE1358 (37° C.) | 0.3277 | 0.3822 | 0.3834 |
| YE1615 (37° C.) | 0.3424 | 0.4077 | 0.4116 |
| Bakers Control (37° C.) | 0.3060 | 0.3060 | 0.3323 |

The amounts of ethanol production (both w/v % and v/v %) at each of 24 hours, 48 hours and 72 hours were calculated. (Table 3). As supported by the weight loss data, both YE1615 and YE1358 yeast strains demonstrated enhanced ethanol production over at least one or both of the analyzed Commercial Yeast Strains at 48 hours at temperatures of 35° C. and 37° C. and 72 hours at temperatures of 30° C., 35° C. and 37° C. Alcohol productions of up to 16.57 v/v % are shown. (Table 3). The demonstrated ethanol concentration from fermentation of YE1615 and YE1358 yeast strains is a function of initial solids loading, wherein the methods of the experiments utilized low initial solids loading (25% as-is weight). Accordingly, the generated ethanol concentration is also lower in respect to commercial or industry standard measurements of ethanol production, as demonstrated by the lower percentages of ethanol production achieved by the tested Commercial Yeast Strains (both Fali and Baker's yeast). The control standards provided by the Commercial Yeast Strains were demonstrated from fermentation at the same initial solids loading (rather than defined conditions such as an initial solids loading as are necessary to generate ethanol production as great as 18% v/v as is often cited by Commercial Yeast Strains). Accordingly, Table 3 shows the differences between the tested strains utilizing the same low initial solids loading.

TABLE 3

| Sample ID | Average 24 Hr. EtOH v/v %* | Average 24 Hr. EtOH w/v %* | Average 48 Hr. EtOH v/v % | Average 48 Hr. EtOH w/v % | Average 72 Hr. EtOH v/v % | Average 72 Hr. EtOH w/v % |
|---|---|---|---|---|---|---|
| Baker's (30° C.) | 15.38 | 12.13 | 15.86 | 12.51 | 16.02 | 12.64 |
| Fali (30° C.) | 15.49 | 12.22 | 15.74 | 12.42 | 15.81 | 12.47 |
| YE 1358 (30° C.) | 10.15 | 8.01 | 15.61 | 12.32 | 15.95 | 12.58 |
| YE 1615 (30° C.) | 13.35 | 10.53 | 15.79 | 12.46 | 15.98 | 12.61 |
| Bakers (35° C.) | 14.72 | 11.61 | 15.86 | 12.51 | 16.08 | 12.69 |
| Fali (35° C.) | 16.00 | 12.62 | 16.28 | 12.84 | 16.36 | 12.91 |
| YE 1358 (35° C.) | 13.98 | 11.03 | 16.27 | 12.84 | 16.42 | 12.96 |
| YE 1615 (35° C.) | 13.50 | 10.65 | 16.20 | 12.78 | 16.46 | 12.99 |
| Baker's (37° C.) | 13.45 | 10.61 | 14.18 | 11.19 | 14.21 | 11.21 |
| Fali (37° C.) | 15.69 | 12.38 | 16.26 | 12.83 | 16.26 | 12.83 |
| YE 1358 (37° C.) | 13.68 | 10.79 | 15.58 | 12.29 | 15.62 | 12.32 |
| YE 1615 (37° C.) | 14.20 | 11.20 | 16.44 | 12.97 | 16.57 | 13.07 |
| Bakers Control (37° C.) | 12.90 | 10.18 | 13.72 | 10.83 | 13.85 | 10.93 |

Figure 5:
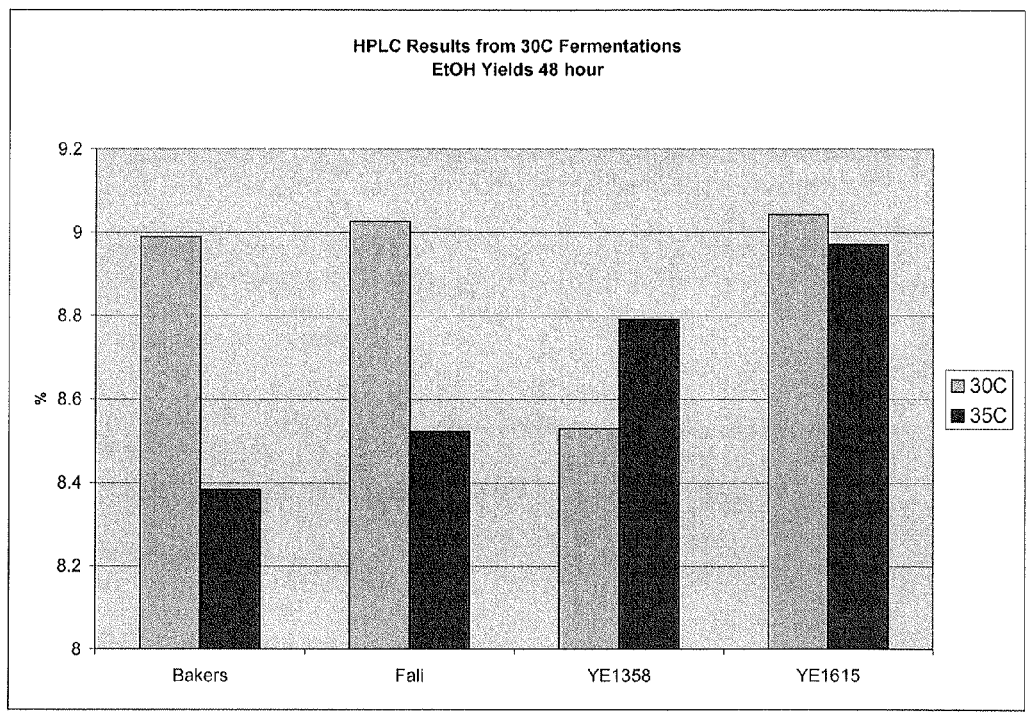
FIG. 5 shows ethanol production of selected yeasts.
Figure 6A:
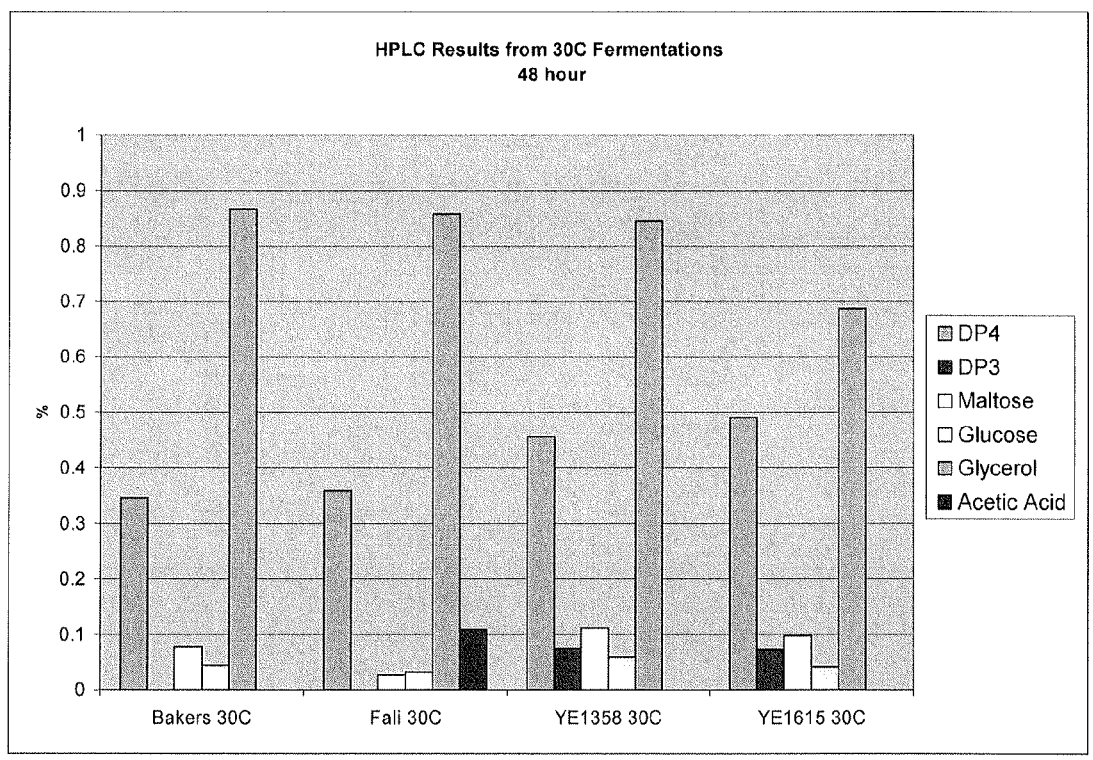
FIGS. 6A-6B show HPLC analysis of yeast fermentations via the conventional starch hydrolysis method.
Figure 6B:
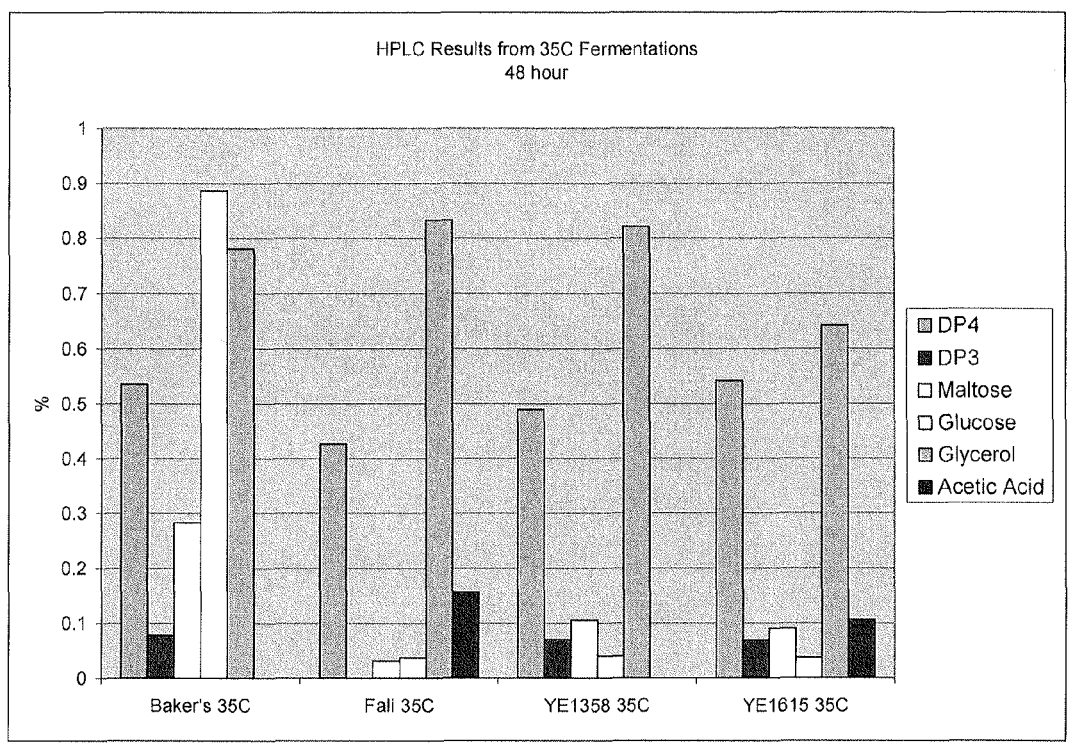

HPLC samples taken at 48 hours showed that the isolated yeast strain YE1615 produced the most ethanol at both 30° C. and 35° C. (FIG. 5). One Commercial Yeast Strain (Fali) had slightly lower residual glucose than the other Commercial Yeast Strain (Baker's), however, both yeast strains YE1615 and YE1358 had residual glucose levels below 1%. Although glycerol levels were low for both yeast strains YE1615 and YE1358, the strain YE1615 demonstrated the lowest level of residual glucose. (FIGS. 6A-6B).

Figure 7:
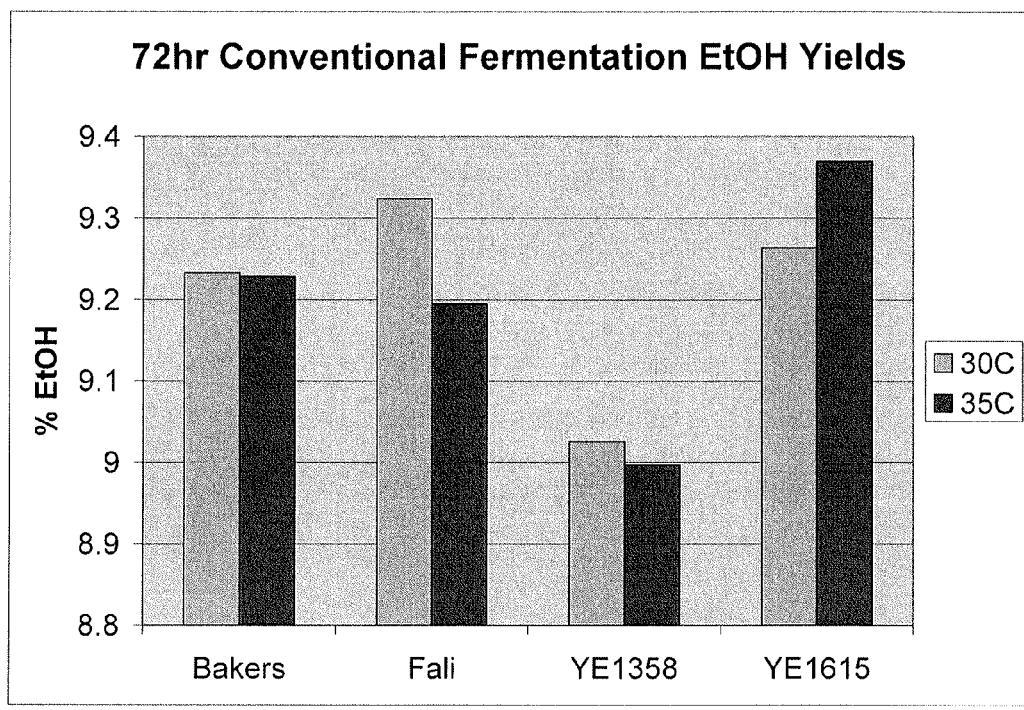
FIG. 7 shows ethanol yields from conventional starch hydrolysis assay of selected yeasts.
Figure 8A:
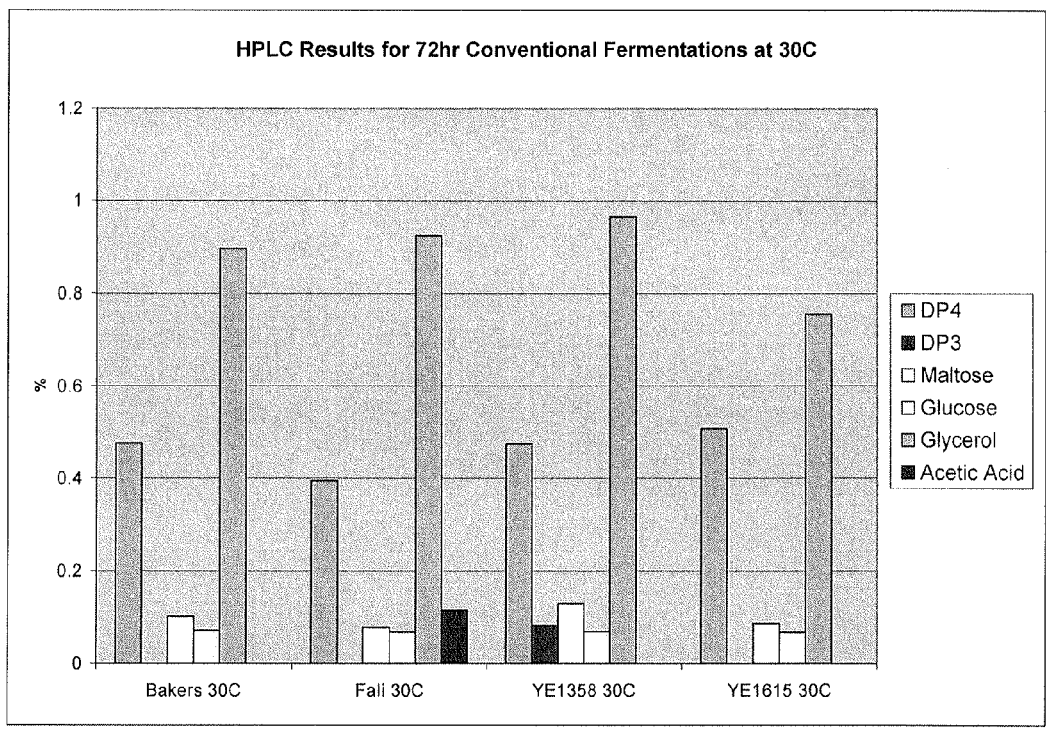
FIGS. 8A-8B show HPLC analysis of selected yeast fermentations via the conventional starch hydrolysis method at various temperatures.
Figure 8B:
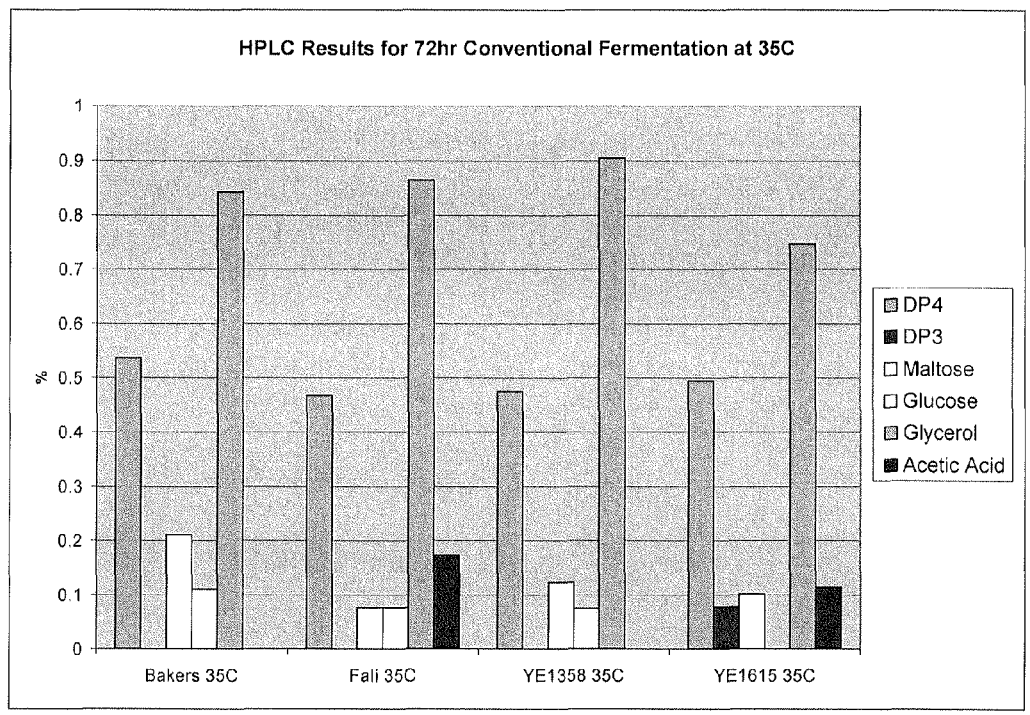

HPLC samples taken at 72 hours showed the YE1615 yeast strain produced slightly less ethanol then one Commercial Yeast Strain (Fali) at 30° C. (FIG. 7). However, the YE1615 yeast strain still had the lowest levels of residual glucose and glycerol at 30° C., despite all residual glucose levels below 1%. (FIG. 8A). Additionally, glycerol levels were low for all tested yeasts. At 35° C. the YE1615 yeast strain produced the most ethanol (FIG. 7) and had the lowest levels of residual glucose and glycerol. (FIG. 8B).

The various modifications of the embodiments of the invention, in addition to those shown and described herein, will be apparent to those skilled in the art from the foregoing description and Examples. Such modifications are also intended to fall within the spirit and scope of the appended claims.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

That which is claimed:

1. A method for producing ethanol comprising culturing *Saccharomyces cerevisiae* strain YE1358 having NRRL Accession No. Y-50432 in a medium comprising a saccharide.

2. The method of claim 1, wherein the *Saccharomyces cerevisiae* strain YE1358 having NRRL Accession No. Y-50432 is capable of increasing ethanol yields when compared to a Commercial Yeast Strain.

3. The method of claim 1, wherein said culturing is at a temperature above 31° C.

4. The method of claim 1, wherein said culturing is at a temperature above 33° C.

5. The method of claim 1, wherein said culturing is at a temperature above 35° C.

6. The method of claim 1, wherein said culturing is at a temperature above 37° C.

7. The method of claim 2, wherein said increased ethanol yield is a yield increase of at least about 1% compared to a Commercial Yeast Strain.

8. The method of claim 2, wherein said increased ethanol yield is a yield increase of at least about 1.5% compared to a Commercial Yeast Strain.

9. The method of claim 1, wherein there is a residua glucose level less than 1%.

10. The method of claim 9, wherein the residual glucose level is less than or equal to about 0.35%.

11. The method of claim 1, wherein said *Saccharomyces cerevisiae* strain YE1358 having NRRL Accession No. Y-50432 is glucose tolerant in glucose concentrations up to at least about 60%.

12. The method of claim 1, wherein said *Saccharomyces cerevisiae* strain YE1358 having NRRL Accession No. Y-50432 is ethanol tolerant in ethanol concentrations up to at least about 25%.

13. The method of claim 12, wherein said *Saccharomyces cerevisiae* strain YE1358 having NRRL Accession No. Y-50432 is ethanol tolerant in ethanol concentrations up to at least about 20% and glucose tolerant in glucose concentrations up to at least about 60%.

14. The method of claim 1 further comprising the steps selected from the group consisting of milling, liquefaction, saccharification, distillation, ethanol extraction and combinations of the same.

15. A method for increasing ethanol production by fermentation comprising culturing *Saccharomyces cerevisiae* strain YE1358 having NRRL Accession No. Y-50432 in a medium comprising a saccharide.

16. The method of claim 15, wherein said ethanol production is increased at least about 1% when compared to fermentation with a Commercial Yeast Strain.

* * * * *